United States Patent [19]

Paulson

[11] Patent Number: 4,796,783
[45] Date of Patent: Jan. 10, 1989

[54] DENTAL FLOSS DISPENSER

[76] Inventor: Ralph E. Paulson, 14802 Grevillea St., Lawndale, Calif. 90260

[21] Appl. No.: 84,976

[22] Filed: Aug. 10, 1987

[51] Int. Cl.⁴ ............................................. B65D 25/38
[52] U.S. Cl. ...................................... 222/80; 222/93; 132/286; 132/325; 206/409; 242/171
[58] Field of Search ............... 222/93, 192; 132/79 E, 132/92 A, 92 R; 242/129.7, 137.1, 138, 139, 170–171; 206/409

[56] References Cited

U.S. PATENT DOCUMENTS

| 664,126 | 12/1900 | Cowan | 132/92 R |
| 911,964 | 2/1909 | Ford | 242/129.7 X |
| 1,488,810 | 4/1924 | Fraser | 132/79 E |
| 1,492,836 | 5/1924 | Decker | 132/79 E |
| 1,733,114 | 10/1929 | Brennan | 132/79 E |
| 1,858,134 | 5/1932 | Booth et al. | 222/93 X |
| 2,983,467 | 5/1961 | Retherford | 206/409 X |
| 4,428,389 | 1/1984 | Cordero | 222/93 X |
| 4,673,106 | 6/1987 | Fishman | 222/391 X |

FOREIGN PATENT DOCUMENTS

| 720710 | 11/1965 | Canada | 242/171 |
| 665460 | 6/1964 | Italy | 222/93 |

*Primary Examiner*—Michael S. Huppert
*Attorney, Agent, or Firm*—Singer & Singer

[57] ABSTRACT

There is described a Dental Floss Disperser located in a unique holder capable of acting as a cap for a conventional tube of tooth paste. The cap contains an internal cylindrical member preferably having threads capable of mating with the threads on a tube of tooth paste. The lower end of the internal cylindrical wall has a shoulder and a disc is slipped over the internal wall and over the shoulder in order to hold the disc in a rotatable relationship. Conventional dental floss is located on the disc and is caused to exit through a small hole in the face portion of the cap. The user of the tube of tooth paste thus has a new cap capable of holding a supply of dental floss. The dispenser not only acts as a cap for a tube of tooth paste but also is capable of being inserted in the bottom end of a conventional pump type tooth paste dispenser thereby allowing the user to have a supply of dental floss contained as part of the pump type tooth paste dispenser.

5 Claims, 1 Drawing Sheet

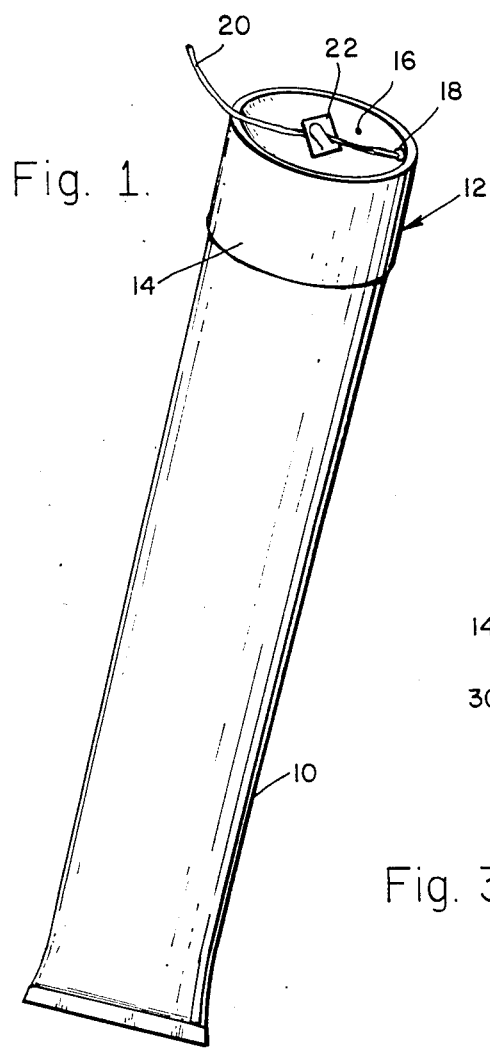
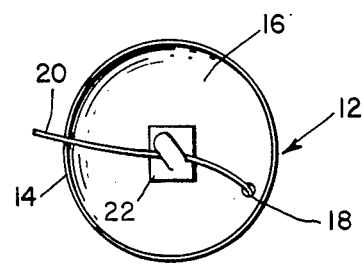
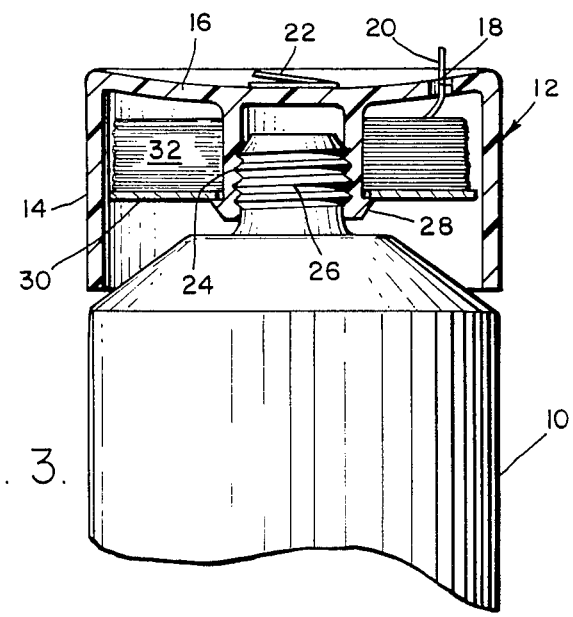
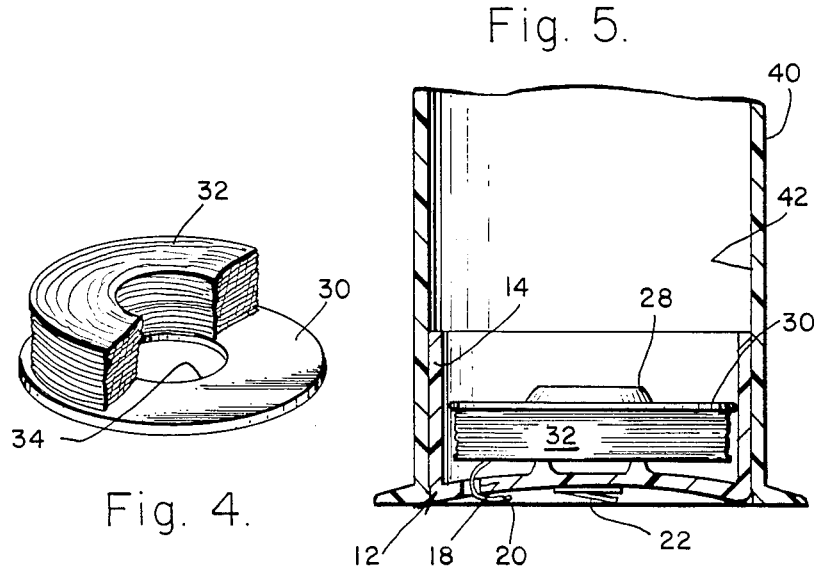

DENTAL FLOSS DISPENSER

This invention relates to a dental floss dispenser and more particularly to a dental floss dispenser capable of being used as a cap for a tube of tooth paste and capable of becoming a integral part of a pump type tooth paste dispenser.

The prior art has recognized that dental floss is an important ingredient in the daily hygienic activities of the individual in cleaning the space between teeth. Typically there are on the market today a plurality of different dental floss dispensers that are sold to the general public and which are intended to be carried by the user in connection with his tooth paste dispenser or his pump dispenser. The typical container for a dental floss dispenser may be round or rectangular or of any shape sufficient only to hold a supply of dental floss capable of being withdrawn and cut into varying lengths dictated only by the needs of the user.

In the tooth paste dispenser art, a tube of tooth paste contains a cap at one end and is constructed of a flexible cover such as plastic, which the user squeezes to remove the tooth paste after the cap has been removed. Upon removing a suitable amount of tooth paste the user replaces the cap and uses the tooth paste on a brush or other means for cleaning his teeth and washing his mouth.

Usually, and at the same time, the user may or may not use his dental floss to clean the space between his teeth of any accumulated debris and in this way hygienically cleans his mouth of odors and foreign particles.

Until the advent of the present invention there was no physical connection between the tooth paste dispenser be it pump type or tube and the dental floss dispenser. It has also been incumbent upon the user to separately carry his tooth paste and his dental floss and hopefully keep both items together so they may both be used at the same time when cleansing his mouth of foreign debris.

The present invention is concerned with a new and novel dental floss dispenser that serves the dual purpose of dispensing dental floss and also serves the purpose of being a cap to a conventional tube of tooth paste. In this fashion the user simply has to carry a single product namely the tooth paste with the dental floss dispenser cap attached and the problem of misplacing or losing the dental floss at the time the user brushes this teeth is minimized. The dental floss dispenser has a novel shape and design that allows it to be used with a tooth paste pump dispenser by inserting the cap in the bottommost portion of the tooth paste pump dispenser thereby creating a single entity for dispensing both tooth paste and dental floss.

In the practice of the present invention there is described a dental floss dispenser that comprises an external thin walled cylindrical member covered at one end with a substantially solid face and having a single opening along the periphery that is adapted to dispense dental floss. Located within the external member is a smaller diameter internal cylindrical member co-axial with the external member and connected at one end to the inside surface of the solid face and terminating at the other end with a shoulder having a diameter that is slightly larger then the external diameter of the internal member. In the preferred embodiment the internal diameter of the smaller internal member is threaded and contains the same pitch diameter as that contained on a conventional tube of tooth paste. The length of the internal member is usually less than the length of the external member.

A coil of dental floss is located on a flat cylindrical disc member which contains a central opening that has a diameter that is greater than the external diameter of the internal member but less than the diameter of the shoulder which is located on the end portion of the internal member. The flat disc member is inserted within the external cylindrical member and over the shoulder on the internal member for holding the flat member in a rotatable relationship. The free end of the dental floss is passed through the opening on the periphery of the front face and is available for use by the customer.

In the preferred embodiment the complete dental floss dispenser is then screwed on top of a conventional tube of tooth paste whereby the threads on the tooth paste tube mate with the threads on the internal surface of the smaller diameter of the internal member thereby allowing the dental floss dispenser to act as a cap for the tube of tooth paste and at the same time allow the user to dispense as much or as little dental floss through the hole in the front cover of the external member.

Further objects and advantages of the present invention will be made more apparent by referring know to the accompaning drawing wherein:

FIG. 1 is a perspective drawing illustrating a conventional tube of tooth paste having a dental floss dispenser cap constructed according to the present invention;

FIG. 2 is a top plan view of the drawing illustrated in FIG. 1;

FIG. 3 is a partial cross sectional view of the dental floss dispenser illustrated in FIGS. 1 and 2;

FIG. 4 illustrates a rotatable disc member holding a coil of dental floss; and

FIG. 5 is a partial cross sectional view of a tooth paste pump dispenser containing the dental floss dispenser constructed according to the teachings of the present invention.

Referring now to FIGS. 1 and 2 there is shown a conventional tube of tooth paste 10 having a dental floss dispenser cap 12 constructed according to teachings of the present invention. The cap 12 is comprised of a thin wall cylindrical member 14 having a concave face 16. Located on the periphery of the face 16 is an opening 18 for allowing dental floss 20 to be passed therethrough. In the preferred embodiment a cutting device 22 is located on the lower most portion of the concave surface of the face 16 and is used to cut the dental floss 20 into preferred lengths by the user.

Referring now to FIG. 3 there is shown a partial cross-sectional view of the dental floss dispenser cap 12 located on top of the tube of tooth paste 10.

The cap 12 is comprised of a substantially thin wall cylindrical member 14 having a given diameter that is approximately the diameter of the tube of tooth paste 10. Located within the external cylindrical member defined by walls 14 is an internal cylindrical member 24 preferably having threads 26 on the internal surface and terminating with a shoulder 28 that has a diameter that is greater than the external diameter of the internal member 24.

Referring now to FIGS. 3 and 4 there is shown a rotatable flat disc 30 located within the external member 14 and containing a coil of dental floss 32.

In the preferred embodiment the disc 30 has a hollow central portion 34 having a diameter that is less than the diameter of the shoulder 28 on the internal member 24 and at the same time the diameter is greater than the external diameter of the internal member 24 thereby allowing the disc 30 to be inserted within the external member 14 and held in place by means of the pretruding shoulder 28. In this fashion the disc 30 is maintained in a rotatable relationship within the dental floss dispenser cap 12 by means of the shoulder 28 located on the internal cylindrical member. One end of the dental floss 20 is threaded through the opening 18 located on the face 16 of the cap 12.

The cap 12 is used as a conventional cap to cover the top of the tooth paste tube 10 and at the same time allows the user to dispense the dental floss 32 through the opening 18 on the face 16. In the preferred embodiment the cutting device 22 is located in the lower most portion of the concave structure of the face 16 so as to provide minimum interference with other items in close proximity to the cap 12.

Referring now to FIG. 5 there is shown a partial cross-sectional view of a pump type dispenser tube 40. The operation of the pump tube is conventional and allows the user to simply push a pump operating lever to dispense a suitable amount of tooth paste for use as dictated by the means of the user. The bottommost portion of the dispensing pump 40 contains a suitable opening 42 into which the dental floss dispenser 12 is inserted. The external thin walled cylindrical member 14 being thin walled is also flexible thereby allowing the user to insert the cap 12 within the opening of the pump 40. In this fashion the operation of the pump is not impeded or changed and the user now has a convenient means of dispensing dental floss in the same fashion as described in connection with FIGS. 1, 2, 3 and 4.

The dental floss dispenser described in connection with the present invention may be used with a tube of tooth paste or with a pump type tube or with neither depending only upon the needs of the user. For example, should the user use the dental floss dispenser as a cap on a tube of tooth paste then it is a simple matter for the user to remove the cap when the tube of tooth paste is empty. The cap may be used as a discreet portion and used only as a dispenser of dental floss or the user may place the cap on another tooth paste tube depending only on the needs of the user.

I claim:

1. A dental floss dispenser comprising:

an external thin walled substantially cylindrical member having a given diameter and covered at on end with a substantially solid face having a single opening, a smaller diameter internal cylindrical member located within and co-axial with said external member and connected at one end to said solid face and terminating at the other end with a shoulder, the length of said internal member being less then the length of said external member, a rotatable hollow disc adapted to be inserted within said external member and having an internal diameter that is greater then the external diameter of said internal member but less then the diameter of said shoulder and an external diameter that is less then the internal diameter of said external member, said disc located within said external member whereby said shoulder on said internal member holds and supports said disc in a rotatable relationship, and a coil of dental floss located on said disc within said external member and with one end of said dental floss extending through said opening on said face.

2. A dental floss dispenser according to claim 1 in which the external surface of said face is concave.

3. A dental floss dispenser according to claim 2 which includes a cutting edge located substantially at the center of said concave surface.

4. A dental floss dispenser according to claim 1 in which said opening is located close to the periphery of said face whereby egress of the dental floss is facilitated.

5. A dental floss dispenser according to claim 1 in which the thin walled external member is flexible and adaptable to be inserted within the bottommost portion of a pump type toothpaste dispenser.

* * * * *